(12) United States Patent
You et al.

(10) Patent No.: US 8,586,540 B2
(45) Date of Patent: Nov. 19, 2013

(54) COMPOSITION FOR IMPROVING SKIN CONDITIONS USING FETAL MESENCHYMAL STEM CELLS FROM AMNIOTIC FLUID

(75) Inventors: Seungkwon You, Gyeonggi-do (KR); Byung Sun Yoon, Seoul (KR); Jai-Hee Moon, Seoul (KR); Eun Kyoung Jun, Gyeonggi-do (KR); Jonggun Kim, Seoul (KR); Hye-Youn Jung, Daejon (KR); Jung Han Lee, Seoul (KR); Eulsoon Park, Seoul (KR); Isaac Maeng, Gyeonggi-do (KR); Jun Sung Kim, Gyeonggi-do (KR); Jang Ho Lee, Seoul (KR); Hwang Heui Lee, Seoul (KR); Jong Won Lee, Gyeonggi-do (KR); Kyoung Shik Cho, Seoul (KR)

(73) Assignee: Stemmedience Co., Ltd. (KR)

( * ) Notice: Subject to any disclaimer, the term of this patent is extended or adjusted under 35 U.S.C. 154(b) by 0 days.

(21) Appl. No.: 13/257,623

(22) PCT Filed: Mar. 19, 2010

(86) PCT No.: PCT/KR2010/001729
§ 371 (c)(1),
(2), (4) Date: Nov. 1, 2011

(87) PCT Pub. No.: WO2010/107286
PCT Pub. Date: Sep. 23, 2010

(65) Prior Publication Data
US 2012/0141399 A1    Jun. 7, 2012

(30) Foreign Application Priority Data
Mar. 20, 2009 (KR) .................. 10-2009-0024055

(51) Int. Cl.
  *A61K 38/00* (2006.01)
  *A61K 38/18* (2006.01)
  *A61P 17/00* (2006.01)
  *A61P 17/02* (2006.01)
  *C07K 14/475* (2006.01)

(52) U.S. Cl.
  USPC .................. 514/18.6; 514/7.6; 514/18.8

(58) Field of Classification Search
  None
  See application file for complete search history.

(56) References Cited

U.S. PATENT DOCUMENTS

| 6,372,494 | B1* | 4/2002 | Naughton et al. ........... 435/391 |
| 2005/0205498 | A1 | 9/2005 | Sowemino-Coker |
| 2007/0065415 | A1 | 3/2007 | Kleinsek |
| 2009/0035283 | A1 | 2/2009 | Park |
| 2009/0136459 | A1* | 5/2009 | Wu et al. ................ 424/93.7 |
| 2011/0177015 | A1* | 7/2011 | Friedlander ............. 424/70.1 |

FOREIGN PATENT DOCUMENTS

KR    1020080063406 A    7/2008

OTHER PUBLICATIONS

Kleinsek et al.*
Roubelakis et al. Stem Cells and Development. Dec. 2007, 16(6): 931-952.*
International Search Report and Written Opinion from PCT/KR2010/001729, dated Nov. 26, 2010.
Guilak et al., "Clonal Analysis of the Differentiation Potential of Human Adipose-Derived Adult Stem Cells", Journal of Cellular Physiology 206: 229-237 (2006).
Gussoni et al., "Dystrophin expression in the mdx mouse restored by stem cell transplantation", Nature, vol. 401, Sep. 23, 1999, p. 390-394.
Jackson et al., "Hematopoietic potential of stem cells isolated from murine skeletal muscle", PNAS, Dec. 7, 1999, vol. 96, No. 25, p. 14482-14486.
Pittenger et al., Multilineage Potential of Adult Human Mesenchymal Stem Cells, Science, vol. 284, Apr. 2, 1999, p. 143-147.
Prockop et al., "Marrow Stromal Cells as Stem Cells for Nonhematopoietic Tissues", Science, vol. 276, Apr. 4, 1997, p. 71-74.
Weissman, "Translating Stem and Progenitor Cell Biology to the Clinic: Barriers and Opportunities", Science, vol. 287, Feb. 25, 2000, p. 1442-1446.
Zuk et al., "Multilineage Cells from Human Adipose Tissue: Implications for Cell-Based Therapies", Tissue Engineering, vol. 7, No. 2, 2001; p. 211-228.
Chen Qiang, et. al. "Surface Instillation of Stem Cell Culture in Repair of Severe Skin Trauma in Guinea Pigs" Chinese Journal of Clinical Rehabilitation, 2005, vol. 9, pp. 228-229.

* cited by examiner

*Primary Examiner* — Daniel C Gamett
(74) *Attorney, Agent, or Firm* — Lathrop & Gage LLP; Brian C. Trinque, Esq.; Andrew T. Wilkins, Esq.

(57) ABSTRACT

The present invention relates to a culture medium for the fetus-derived mesenchymal stem cells in amniotic fluid. More particularly, the present invention relates to a composition for improving skin conditions, comprising the culture medium of fetus-derived mesenchymal stem cells in amniotic fluid as an active ingredient, in which the skin conditions to be improved include whitening, wrinkles, skin damages caused by UV rays or skin lifting. Further, the present invention relates to a method for preparing the composition, comprising the steps of culturing the fetus-derived mesenchymal stem cells in amniotic fluid; and collecting the culture medium.

7 Claims, 13 Drawing Sheets

(a)

(b)

(a)

(b)

_US 8,586,540 B2_

COMPOSITION FOR IMPROVING SKIN CONDITIONS USING FETAL MESENCHYMAL STEM CELLS FROM AMNIOTIC FLUID

The present application claims the benefit of priority of International Application No. PCT/KR2010/001729, filed Mar. 19, 2010, which claims priority to Korean Patent Application No. 10-2009-0024055, filed Mar. 20, 2009. The entire contents of each of the above documents are incorporated herein by reference.

BACKGROUND OF THE INVENTION

1. Field of the Invention

The present invention relates to a culture medium for the fetus-derived mesenchymal stem cells in amniotic fluid. More particularly, the present invention relates to a composition for improving skin conditions, comprising the culture medium of the fetus-derived mesenchymal stem cells in amniotic fluid as an active ingredient, in which the skin conditions include whitening, wrinkles, skin damages caused by UV rays or skin lifting. Further, the present invention relates to a method for preparing the composition, comprising the steps of culturing the fetus-derived mesenchymal stem cells in amniotic fluid; and collecting the culture medium.

2. Description of the Related Art

Stem cells have an ability to differentiate into a variety of cells by appropriate environment and stimulation and also have a self-proliferating ability. There are three types of stem cells: embryonic stem cells (ES cells) isolated from the early embryo, embryonic germ cells (EG cells) isolated from primordial germ cells at an embryonic stage, and multipotent adult progenitor cells (MAPC cells) isolated from adult bone marrow. Stem cells have the potential to develop into cells that have unique phenomena and specialized functions, and thus they have been proposed as an attractive cell source for regenerating various organs.

Until now, adult stem cells have been known to have the ability to differentiate into various cells. Adult stem cells were isolated from the bone marrow (Science 276, 71-74, 1997; Science 284, 143-147, 1999; Science 287, 1442-1446, 2000), the skeletal muscle (Proc. Natl Acad. Sci. USA 96, 14482-14486, 1999; Nature 401, 390-394, 1999), and the fat tissue (Tissue Eng 7, 211-228, 2001; J. Cell. Physiol. 206, 229-237, 2006), and each of them is able to differentiate into similar cell lineages.

Bone marrow-derived mesenchymal stem cells are adult stem cells that have been used for a long time, and their efficacies were also proved. In addition, recent studies have reported that the cells isolated from fat tissue or other tissues also have similar characteristics to the bone marrow-derived mesenchymal stem cells. However, it is difficult to isolate and purify a large amount of mesenchymal stem cells, and thus other alternative sources are urgently needed.

Therefore, the present inventors have focused on amniotic fluid that can be easily separated without any risk to the baby or its mother.

A few days after implantation of the fertilized egg to the uterine wall, the embryo is surrounded by the amniotic sac filled with amniotic fluid. Since the amniotic fluid contains a lot of materials excreted by the fetus, chromosome abnormalities of the fetus or bacterial infection can be tested in the amniotic fluid. In addition, amniotic fluid allows for easier fetal movement, protects the fetus from any outside impact and stimulation, prevents bacterial infection, and helps to regulate the fetal body temperature.

Before birth, information about the fetal health can be obtained through examination of the amniotic fluid. At this time, amniotic fluid can be collected throughout pregnancy without any risk to the mother. The cells used in the examination are discarded after examination, and can be used for research purposes under the patient's consent. Therefore, amniotic fluid-derived stem cells possess an advantage over other adult stem cells, because a large amount of cells can be easily obtained. At present, there are no reports whether the addition of a medium, obtained by culturing the fetus-derived mesenchymal stem cells in amniotic fluid for a predetermined period, affects the growth of fibroblasts.

The present inventors have isolated mesenchymal stem cells from the fetus in amniotic fluid and investigated their characteristics. Further, they have investigated components present in a conditioned medium that is prepared using the fetus-derived mesenchymal stem cells in amniotic fluid, and demonstrated effects of the conditioned medium in fibroblasts. Furthermore, the present inventors have demonstrated effects of the conditioned medium composition on skin elasticity and regeneration through a mouse in vivo test and a clinical test, thereby completing the present invention.

SUMMARY OF THE INVENTION

An object of the present invention is to provide a composition for improving skin conditions, comprising the culture medium of the fetus-derived mesenchymal stem cells in amniotic fluid as an active ingredient.

Another object of the present invention is to provide a method for preparing the composition, comprising the steps of culturing the fetus-derived mesenchymal stem cells in amniotic fluid; and collecting the culture medium.

DETAILED DESCRIPTION OF THE PREFERRED EMBODIMENTS

In order to achieve the above objects, one embodiment of the present invention relates to a composition for improving skin conditions, comprising the culture medium of the fetus-derived mesenchymal stem cells in amniotic fluid as an active ingredient, in which the skin conditions include whitening, wrinkles, skin damages caused by UV rays or skin lifting.

As used herein, the term "mesenchymal, stem cells (MSCs)" refers to cells that differentiate into the cartilage, bone, fat, bone marrow stroma, muscle, nerve or the like, and are mostly present in the adult bone marrow, but also found in umbilical cord blood, peripheral blood, other tissues or the like, and they can be obtained therefrom. With respect to the objects of the present invention, the mesenchymal stem cells of the present invention mean the fetus-derived mesenchymal stem cells in amniotic fluid.

Various chemicals excreted from the fetus are included in the amniotic fluid from a pregnant woman, and they can produce most cells in the body, and be easily collected. In addition, heterogeneous populations of cells are present in the amniotic fluid, and the present inventors identified the presence of a homogeneous population of mesenchymal stem cells having a fibroblast-like morphology which is a characteristic of mesenchymal stem cells.

The present invention is characterized in that the cells in the amniotic fluid are derived from the fetus.

Figure 2:
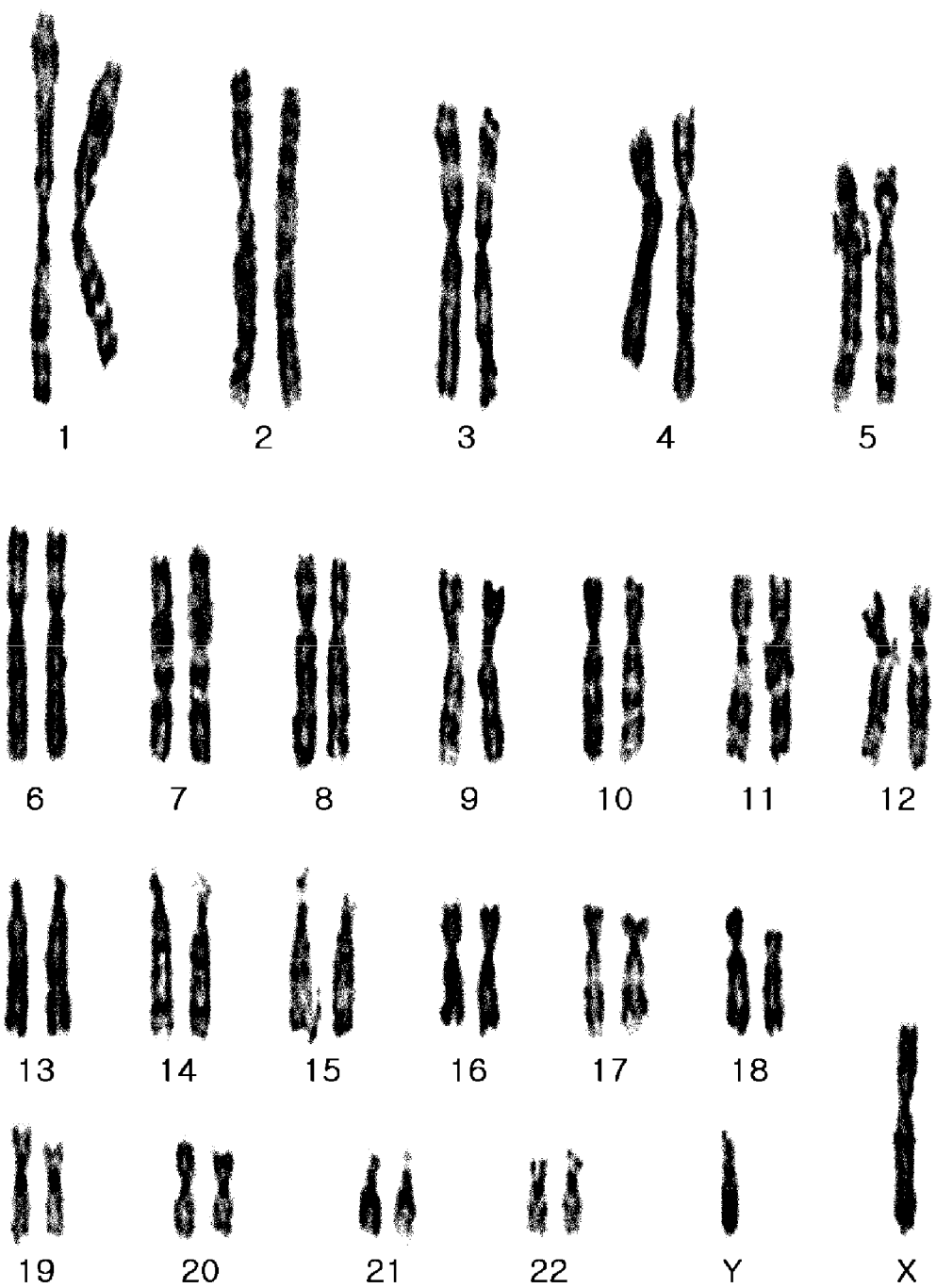
FIG. 2 shows the result of karyotyping the fetus-derived cells in amniotic fluid that is isolated from the mother, in which sex chromosomes of XY indicate that the cells are derived from the fetus in amniotic fluid, not the mother.

In the preferred embodiment of the present invention, karyotyping is performed to confirm whether the cells in the amniotic fluid are derived from the fetus. In the amniotic fluid, some of the mother's cells are also present, as well as fetal cells. In the present invention, chromosome analysis was performed to detect male, indicating that the cells in the amniotic fluid are derived from the fetus (FIG. 2).

Preferably, the composition of the present invention includes Apo-1/Fas, epidermal growth factor (EGF), IP-10, leptin, MIP4, MMP3, Rantes, interferon-gamma (IFNγ), human transforming growth factor (TGF-β), tumor necrosis factor-alpha (TNFα), tumor necrosis factor receptor I (TNFRI), tumor necrosis factor receptor II (TNFRII), intracellular adhesion molecule-1 (ICAM-1), vascular cell adhesion molecule-1 (VCAM-1), vascular endothelial growth factor (VEGF), interleukin-1beta (IL-1β), interleukin-1 receptor alpha (IL-1Rα), IL-2, IL-3, IL-4, IL-5, IL-6, IL-6R, IL-7, IL-8, IL-12 and IL-15.

Further, the fetus-derived mesenchymal stem cells in amniotic fluid, prepared by the method of the present invention, are characterized by showing (a) the immunological characteristics of being all positive for CD13, CD29 and CD44, (b) growing and adhering to cell culture plates and showing a spindle-shaped morphology which is a typical fibroblast morphology, and (c) having a capacity to differentiate into mesodermal cell lineages.

As used herein, the term "differentiation" refers to a phenomenon in which the structure or function of cells is specialized during the division, proliferation and growth thereof. Pluripotent mesenchymal stem cells give rise to progenitor cells that differentiate into committed cell lineages (e.g., mesodermal cells), and may further differentiate into other types of progenitor cells (e.g., osteoblast, etc.), which in turn generate terminally differentiated cell types (e.g., adipocytes, osteoblasts, chondrocytes, etc.) that have specialized functions in the specialized tissues (e.g., bone, etc.). In the preferred embodiment, the fetus-derived mesenchymal stem cells in amniotic fluid of the present invention have a capacity to differentiate into adipocytes, osteoblasts and chondrocytes.

In the specific Example of the present invention, a medium for differentiation into the adipocytes may include high glucose DMEM, 1 mM dexamethasone, 0.5 mM 3-isobutyl-1-methyl-caffeine (3-isobutyl-1-methyl-xanthine), 10 ng/ml insulin, 100 mM indomethacin, and 10% FBS.

In the specific Example of the present invention, a medium for differentiation into the osteoblasts may include high glucose DMEM, 100 mM dexamethasone, 10 mM β-glycerophosphate, 0.2 mM ascorbate and 10% FBS.

In the specific Example of the present invention, a medium for differentiation into the chondrocytes may include high glucose DMEM, 0.1 M dexamethasone, 50 g/ml AsA, 100 g/ml sodium pyruvate, 40 g/ml proline, 10 ng/ml TGF-1 and 50 mg/ml ITS premix [6.25 g/ml insulin, 6.25 g/ml transferrin, 6.25 g/ml selenius acid, 1.25 mg/ml BSA and 5.35 mg/ml linoleic acid].

Figure 4:
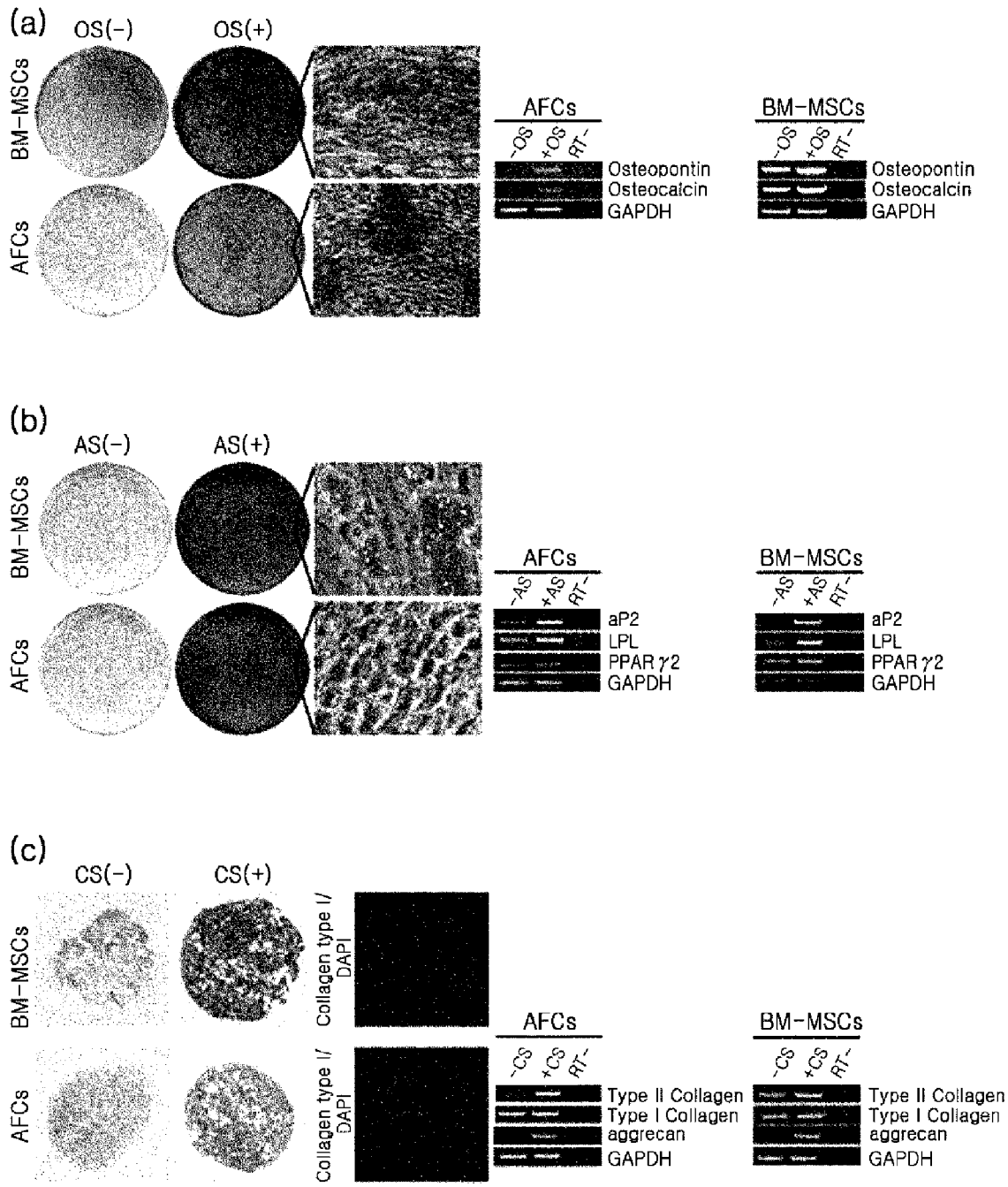
FIG. 4 shows adipogenic differentiation (A), osteogenic differentiation (B), and chondrogenic differentiation (C) of the fetus-derived cells in amniotic fluid, indicating that the cells have similar differentiation capacity to the pluripotent bone marrow-derived mesenchymal stem cells.

In the present invention, the fetus-derived mesenchymal stem cells in amniotic fluid were cultured in the media for each differentiation for 7 to 28 days. By this method, it can be demonstrated whether the fetus-derived cells in amniotic fluid have the characteristics of mesenchymal stem cells (FIG. 4). Therefore, in the present invention, the fetus-derived cells in amniotic fluid are cells having the characteristics of mesenchymal stem cells, and can be used as a source of other cells as well as bone marrow.

The composition of the present invention shows effects of improving skin conditions, in particular, whitening, wrinkles, skin damages caused by UV rays, skin regeneration or skin lifting.

Figure 10:
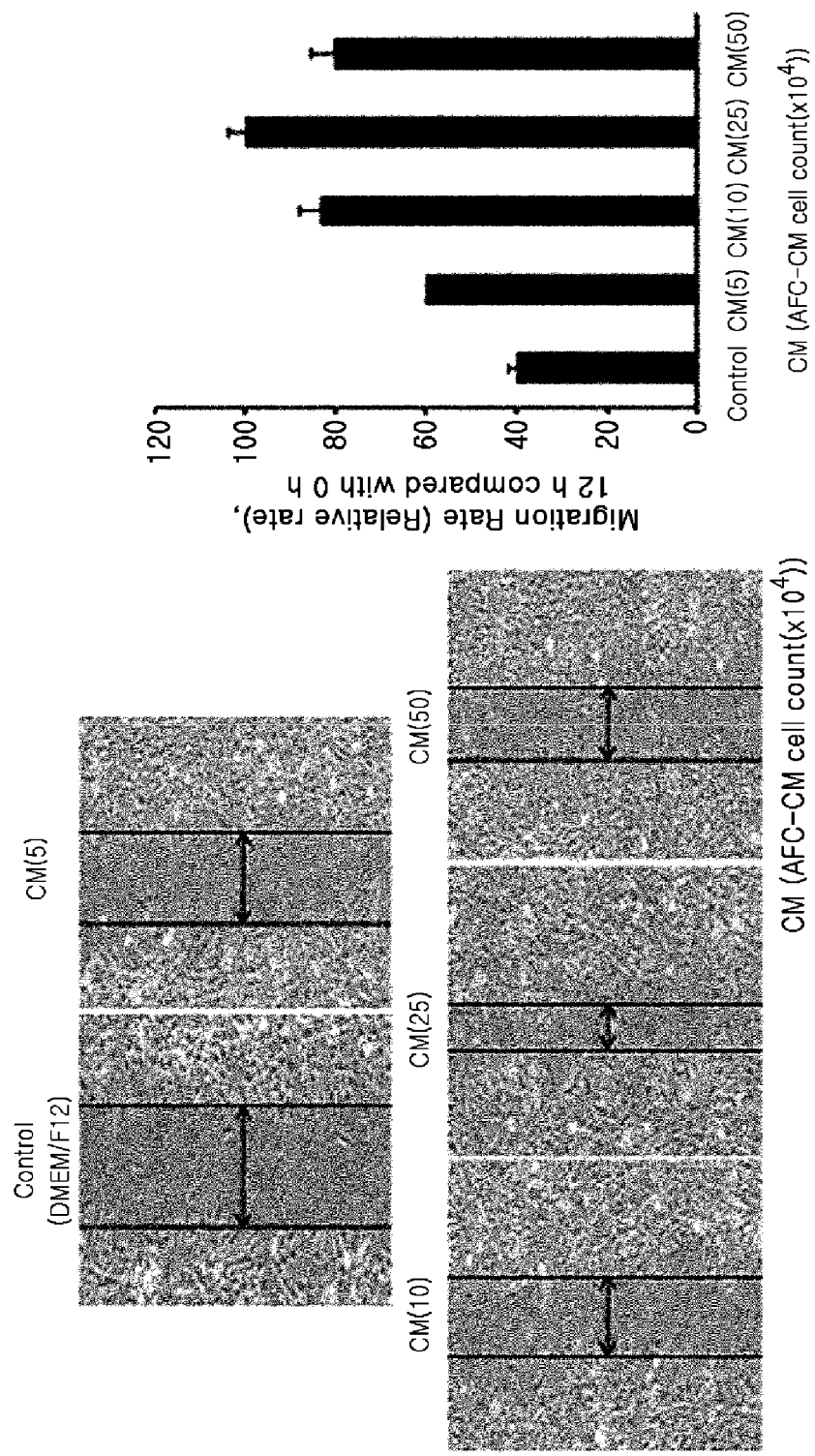
FIGS. 10 to 11 show that the conditioned medium, obtained using the fetus-derived mesenchymal stem cells in amniotic fluid, has the wound healing-effects in the skin fibroblast.
Figure 11:
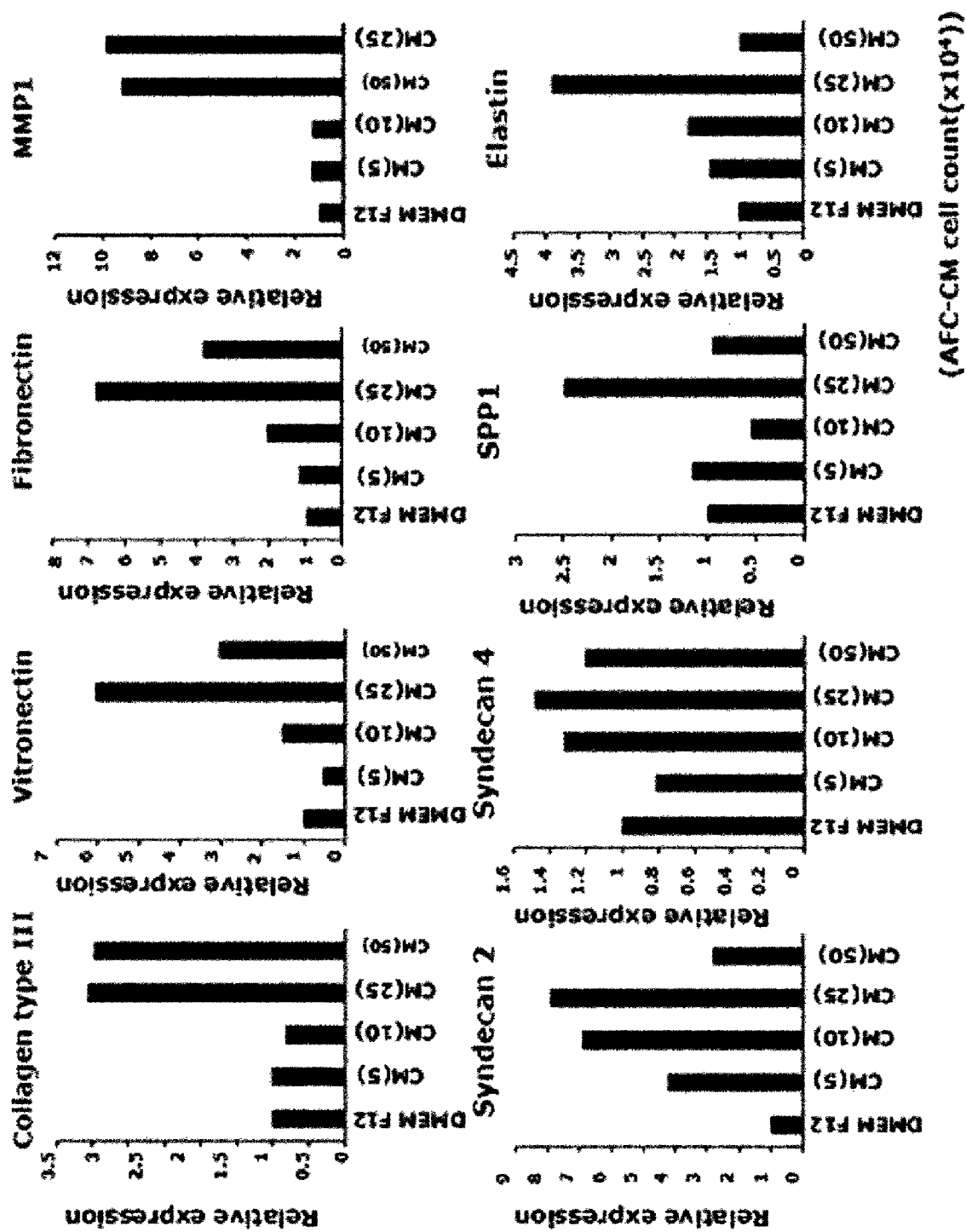

In the specific Example of the present invention, an artificial wound was generated in the skin-derived fibroblasts, and then the cells were treated with the composition of the present invention. The results showed that cell migration was enhanced and the expression of wound healing-related genes was quantitatively increased, indicating excellent wound healing effects (FIGS. 10 to 11).

Figure 12:
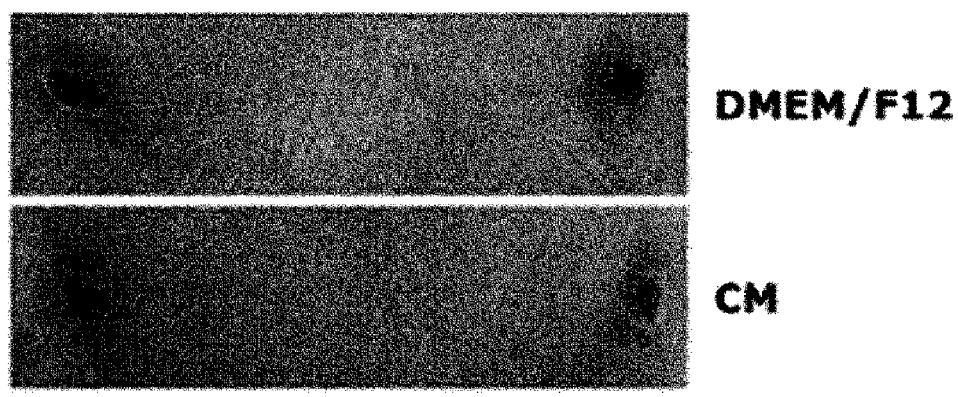
FIG. 12 shows the result of in vivo test, indicating the conditioned medium obtained using the fetus-derived mesenchymal stem cells in amniotic fluid having regeneration effects in the wounded mouse skin.
Figure 12:
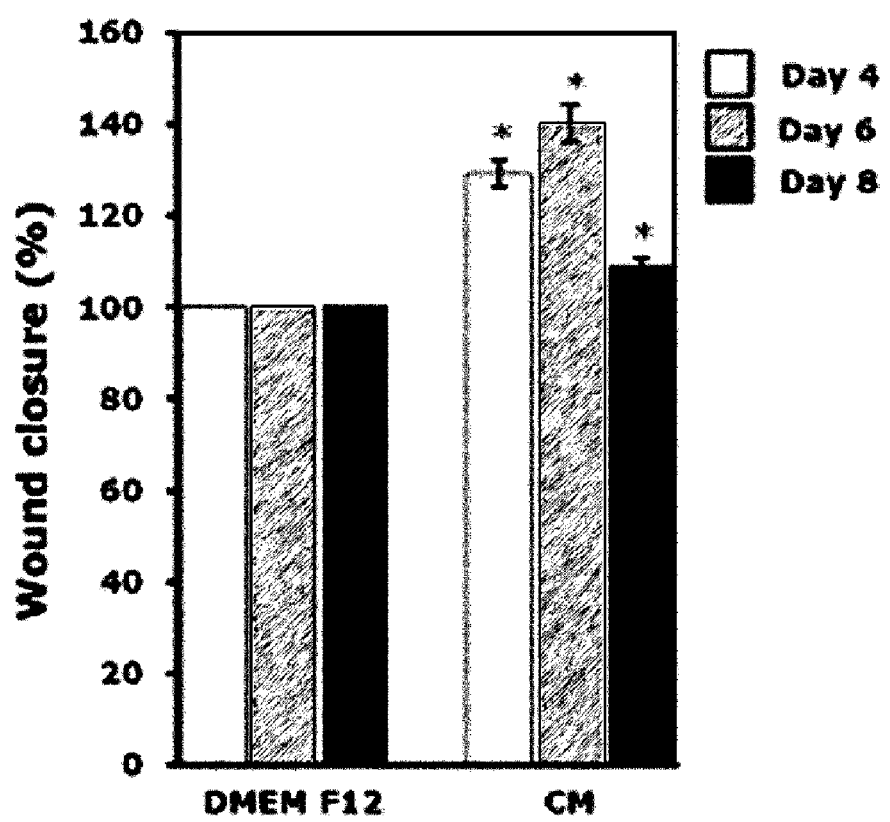

Further, an artificial wound was generated in the mouse skin, and then the composition of the present invention was applied thereto. The results showed that the wound site was gradually reduced, indicating excellent wound closure and skin regeneration effects (FIG. 12).

Further, in the clinical study using the composition of the present invention, when the skin was stimulated using a microneedle after microtherapy of the composition of the present invention, it was found that skin elasticity was improved, skin tone became brighter, and fine wrinkles were reduced, and skin pores were minimized. When the observation was performed in the same manner for 6~7 weeks, the improvement in red-marks of acne scars and the rapid wound regeneration were observed, indicating that the composition of the present invention shows excellent effects of improving whitening, wrinkles, skin damages, skin regeneration and skin lifting (FIG. 12).

According to the preferred embodiment of the present invention, the composition of the present invention is a cosmetic composition.

The ingredients contained in the cosmetic composition of the present invention are effective ingredients, including ingredients commonly used in cosmetic compositions, in addition to the culture medium of the fetus-derived mesenchymal stem cells in amniotic fluid. Such ingredients include, for example, conventional auxiliary agents such as an antioxidant, a stabilizer, a solubilizing agent, a vitamin, a pigment, and a flavor, and a carrier. In addition, the cosmetic composition may further include a skin absorption enhancer in order to promote the effect.

The cosmetic composition of the present invention may be prepared as any formulation commonly prepared in the art. The cosmetic composition may be formulated as, for example, a solution, a suspension, an emulsion, a paste, a gel, a cream, a lotion, a powder, a soap, a surfactant-containing cleanser, an oil, a powdered foundation, an emulsion foundation, a wax foundation, a spray or the like, but is not limited thereto. More specifically, the cosmetic composition may be prepared as a formulation such as a softening toner, a nutrient toner, a nutrient cream, a massage cream, essence, an eye cream, a cleansing cream, a cleansing foam, a cleansing water, a pack, a spray, or a powder. If the formulation of the present invention is a paste, a cream or a gel, animal oil, vegetable oil, wax, paraffin, starch, traganth, cellulose derivatives, polyethylene glycol, silicone, bentonite, silica, talc, zinc oxide or the like may be used as the carrier ingredient.

If the formulation of the present invention is a powder or a spray, lactose, talc, silica, aluminum hydroxide, calcium silicate, or polyamide powders may be used as the carrier ingredient, and in particular, if the formulation is a spray, a propellent such as chlorofluorohydrocarbon, propane/butane or dimethyl ether may be contained. If the formulation of the present invention is a solution or an emulsion, a solvent, a solubilizing agent or an emulsifier may be used as the carrier ingredient, and examples thereof include water, ethanol, isopropanol, ethyl carbonate, ethyl acetate, benzyl alcohol, benzyl benzoate, propylene glycol, 1,3-butylglycol oil, glycerol aliphatic esters, polyethylene glycol or sorbitan fatty acid esters. If the formulation of the present invention is a suspension, a liquid diluent such as water, ethanol and propylene glycol, a suspending agent such as ethoxylated isostearyl alcohol, polyoxyethylene sorbitol ester and polypoxyethylene sorbitan ester, microcrystalline cellulose, aluminum metahydroxide, bentonite, agar, traganth or the like may be used as the carrier ingredient. If the formulation of the present invention is a surfactant-containing cleanser, aliphatic alcohol sulfate, aliphatic alcohol ether sulfate, sulphosuccinic acid monoester, isethionate, imidazolinium derivative, methyltaurate, sarcosinate, fatty acid amide ether sulfate, alkylamidobetain, aliphatic alcohol, fatty acid glyceride, fatty acid diethanolamide, vegetable oils, a lanolin derivative or ethoxylated glycerol fatty acid ester or the like may be used as the carrier ingredient.

Further, the composition of the present may be prepared as a pharmaceutical composition.

If the composition of the present invention is prepared as a pharmaceutical composition, the pharmaceutical composition of the present invention includes a pharmaceutically acceptable carrier. The pharmaceutically acceptable carriers included in the pharmaceutical composition of the present invention are those typically used upon formulation, and include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methylhydroxybenzoate and propylhydroxybenzoate, talc, magnesium stearate and mineral oils, but are not limited thereto. The pharmaceutical composition of the present invention may further include lubricants, wetting agents, sweetening agents, flavoring agents, emulsifying agents, suspending agents, preservatives or the like, in addition to the above ingredients. The suitable pharmaceutically acceptable carriers and formulations are described in Remington's Pharmaceutical Sciences (19$^{th}$ ed., 1995).

The pharmaceutical composition of the present invention may be administered to mammals such as a rat, mouse, livestock, and human via various routes such as oral and parenteral routes, for example, oral, rectal or intravenous, intramuscular, subcutaneous, intraepidural or intracerebrovascular injection, preferably, transcutaneous route among parenteral routes, and more preferably topical application.

A suitable dosage of the pharmaceutical composition of the present invention may be determined depending on various factors such as formulation methods, administration mode, the patient's age, body weight, gender and health state, diet, administration time, administration routes, excretion rates, and drug sensitivity. For oral administration, the pharmaceutical composition of the present invention may be administered at a daily dosage of 0.1-100 mg/kg one time or several times for adults. Further, for topical administration, the pharmaceutical composition of the present invention may be preferably administered at a daily dosage of 1.0 to 3.0 ml one to five times for 1 month or more for adults. However, the scope of the present invention is not intended to be limited by the dosage.

The pharmaceutical composition of the present invention may be formulated into a unit dosage form or a multidose container using the pharmaceutically acceptable carriers and/or excipients according to the methods known to those skilled in the art. The pharmaceutical composition may be formulated into any suitable formulation including oral formulations such as powder, granules, tablets, capsules, suspensions, emulsions, syrup, and aerosol, topic external preparations such as ointment and cream, suppository or sterilized solution for injection. The pharmaceutical formulations may further include a dispersing agent or a stabilizing agent.

Another embodiment of the present invention relates to a method for preparing the composition, comprising the steps of culturing the fetus-derived mesenchymal stem cells in amniotic fluid; and collecting the culture medium.

More preferably, the present invention relates to a method for preparing the composition, comprising the steps of (a) isolating the fetus-derived cells in amniotic fluid that is obtained from a pregnant woman; (b) subculturing the cells in a medium supplemented with FBS and bFGF so as to obtain the fetus-derived mesenchymal stem cells in amniotic fluids; (c) culturing the obtained fetus-derived mesenchymal stem cells in amniotic fluid in a serum-free medium for 1 to 10 days so as to prepare a conditioned medium; and (d) collecting the conditioned culture medium.

In step (a), the amniotic fluid can be collected from the beginning of pregnancy until delivery without any risk to the mother. Informations about the fetal health can be obtained through the examination of the amniotic fluid before birth, and the cells used in the examination are discarded after examination. At this time, the cells can be used for research purposes under the patient's consent. Therefore, a large amount of cells can be easily obtained. The amniotic fluid obtained from the mother is centrifuged to isolate the fetus-derived cells in amniotic fluid.

In step (b), the cells isolated from the amniotic fluid were subcultured so as to obtain the fetus-derived mesenchymal stem cells in the amniotic fluid. The medium used in the subculture is preferably a cell culture minimum medium (CCMM), which generally contains carbon sources, nitrogen sources, and trace elements. Examples of the cell culture minimum medium include DMEM (Dulbecco's Modified Eagle's Medium), MEM (Minimal essential Medium), BME (Basal Medium Eagle), RPMI1640, F-10, F-12, αMEM (α Minimal essential Medium), GMEM (Glasgow's Minimal essential Medium) and IMEM (Iscove's Modified Dulbecco's Medium), but are not limited thereto. In addition, the medium may contain an antibiotic such as penicillin, streptomycin, and gentamicin.

In the present invention, the fetus-derived mesenchymal stem cells in amniotic fluid may be obtained by culturing the cells isolated from amniotic fluid in a basal medium supplemented with FBS and bFGF, and preferably obtained by culturing the cells in a 10% FBS-containing low glucose DMEM medium supplemented with 4 ng/ml bFGF. In the preferred Example of the present invention, the low glucose DMEM medium may further contain 10% FBS, 1% L-glutamine and 1% penicillin-streptomycin, and 4 ng/ml bFGF solution.

In step (c), the obtained fetus-derived mesenchymal stem cells in amniotic fluid were cultured in the serum-free medium for 1 to 10 days so as to prepare a conditioned medium.

As used herein, the term "conditioned medium" refers to a medium prepared by the following procedures: when the suspension-cultured cells reach the logarithmic growth phase, dividing cells are removed by centrifugation or filtration, and the culture medium is only collected and mixed with a culture substrate. This is a method of using unknown growth factors excreted from the dividing cells into the medium, and usually used for plating of cells at low density or for protoplast culture.

With respect to the objects of the present invention, the conditioned medium composition of the present invention refers to a composition containing a solution that is prepared by removing the fetus-derived mesenchymal stem cells from the culture medium of the fetus-derived mesenchymal stem cells, and refers to a composition containing plenty of materials such as growth factors that are derived from the fetus-derived mesenchymal stem cells, and preferably includes Apo-1/Fas, epidermal growth factor (EGF), IP-10 (Interferon-γ inducible protein-10), leptin, MIP4, MMP3, Rantes, interferon-gamma (IFNγ), human transforming growth factor (TGF-β), tumor necrosis factor-alpha (TNFα), tumor necrosis factor receptor I (TNFRI), tumor necrosis factor receptor II (TNFRII), intracellular adhesion molecule-1 (ICAM-1), vascular cell adhesion molecule-1 (VCAM-1), vascular endothelial growth factor (VEGF), interleukin-1beta (IL-1β), interleukin-1 receptor alpha (IL-1Rα), IL-2, IL-3, IL-4, IL-5, IL-6, IL-6R, IL-7, IL-8, IL-12 and IL-15.

In the present invention, in order to obtain the conditioned medium of the fetus-derived mesenchymal stem cells, the mesenchymal stem cells isolated and obtained from the amniotic fluid are preferably cultured in a serum-free medium containing Ham's F-12 nutrient mixture with amino acids or analogs thereof and vitamins or analogs thereof. The serum-free medium containing Ham's F-12 nutrient mixture according to the present invention is based on DMEM without a pH indicator such as phenol red, and Ham's F-12 nutrient mixture is added thereto at a ratio of approximately 1:0.5~2. In this connection, it is possible to add oxidation nutrients such as L-glutamine, energy metabolites such as sodium pyruvate, and carbon sources such as sodium bicarbonate. In this mixture, various inorganic substances and amino acids, which help to maintain the growth and homeostasis of the cells and are involved in increasing the safety and maintenance of the cells in the subculture following the initial-stage culture of the mesenchymal stem cells, vitamin nutrients that can stimulate the higher production of growth factors secreted from the fetus-derived mesenchymal stem cells, and other factors are mixed with each other at a given ratio.

Figure 5:
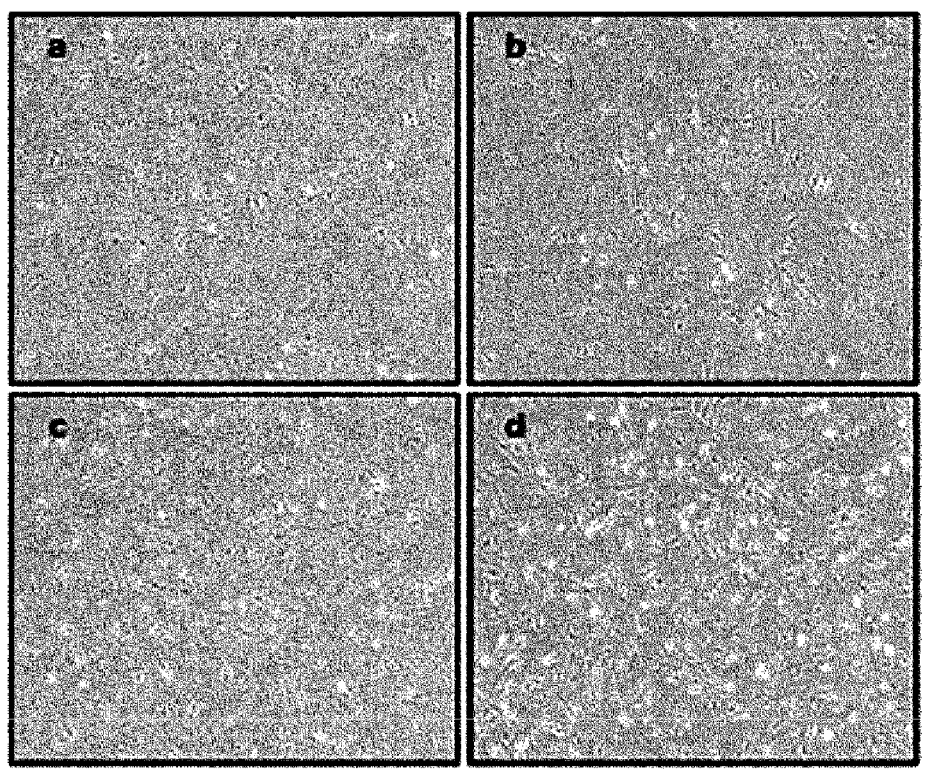
FIG. 5(A) shows the preparation of conditioned medium by using the established fetus-derived mesenchymal stem cells in amniotic fluid and a DMEM/F12-serum free medium, in which $5 \times 10^4$ (a), $1 \times 10^5$ (b), $2.5 \times 10^5$ (c) and $5 \times 10^5$ (d) cells were observed under a microscope.
FIG. 5(B) shows the result of CFU-assay after seeding each cell count per $cm^2$.
Figure 5:
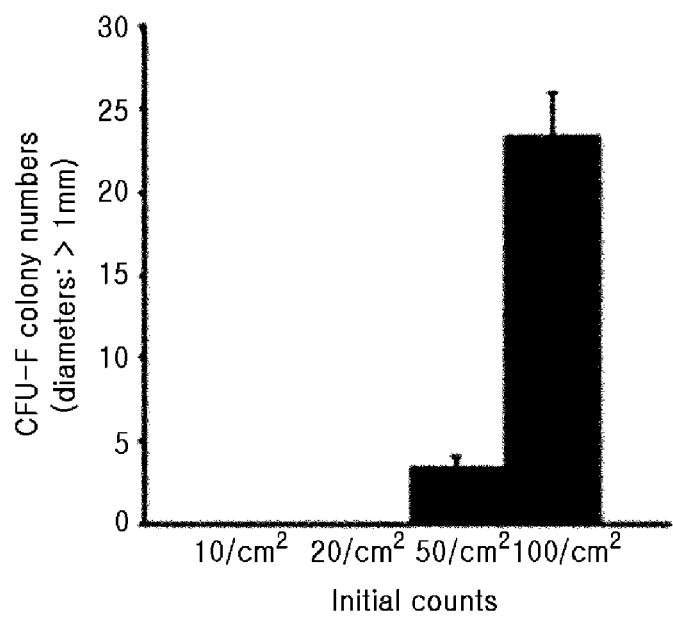

In the specific Example of the present invention, the fetus-derived cells that are isolated in the amniotic fluid obtained from the mother were subcultured in the medium supplemented with FBS and bFGF so as to obtain the fetus-derived mesenchymal stem cells in amniotic fluid. Then, different numbers of the amniotic fluid cells were cultured in a DMEM/F-12 serum-free medium for 3 days, and the obtained culture medium was centrifuged and filtered so as to prepare a conditioned medium (FIG. 5).

In step (d), the conditioned culture medium was collected so as to prepare the composition for improving skin conditions of the present invention. The collection of the conditioned culture medium may be performed by a method known to those in the art, for example, by centrifugation or filtration.

Hereinafter, the present invention will be described in more detail with reference to Examples. However, these Examples are for illustrative purposes only, and the invention is not intended to be limited by these Examples.

EXAMPLE 1

Figure 1:
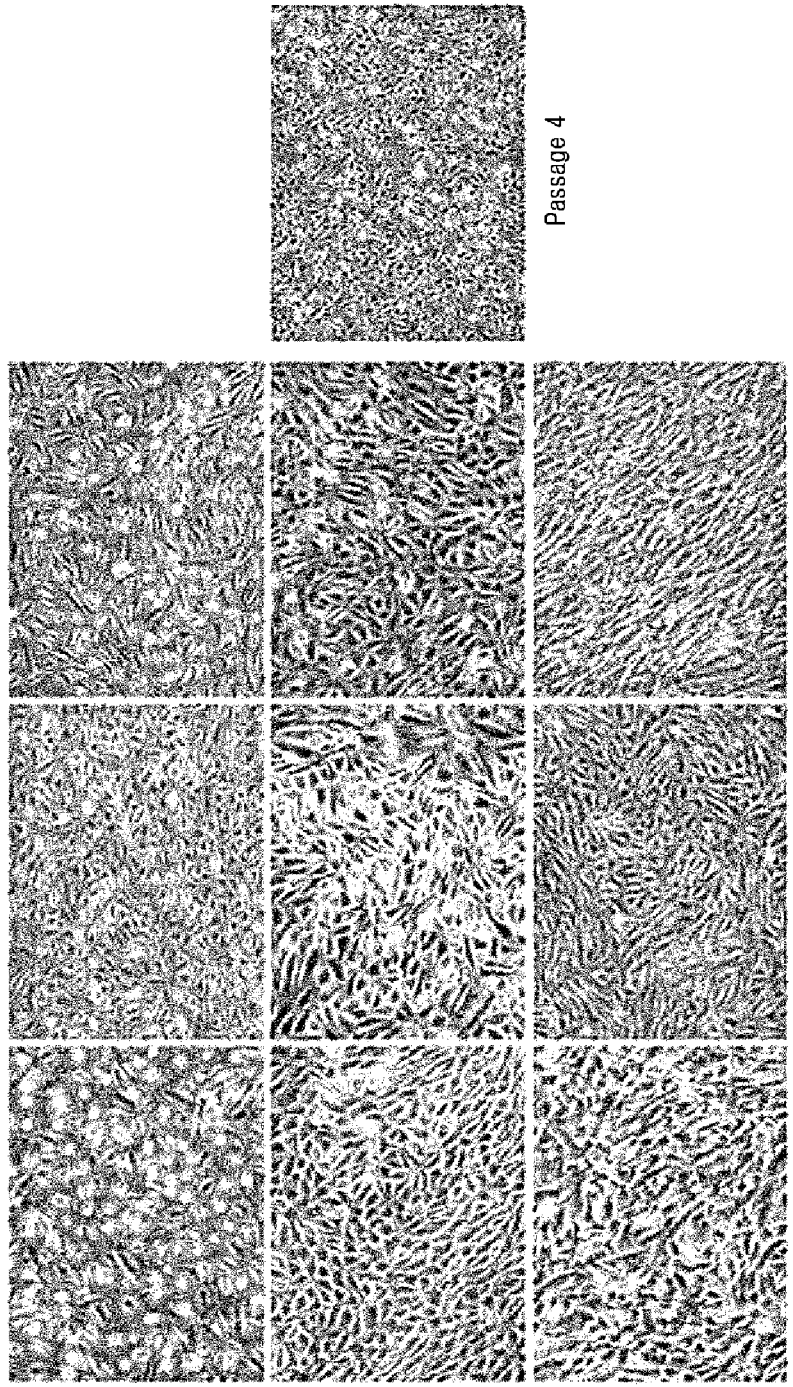
FIG. 1 shows heterogeneous populations (left) of the fetus-derived cell line in amniotic fluid and homogeneous enrichment of mesenchymal stem cells (right: 4 passages) after 2~3 subcultures.

Culture of Fetus-Derived Cell Line in Amniotic Fluid Obtained from Pregnant Woman and Morphology Identification of Homogeneous Mesenchymal Stem Cells Under Culture Conditions There are many floating particles in the amniotic fluid obtained from a pregnant woman. In order to separate them, the amniotic fluid was put in a T-flask and incubated at 37° C. The next day, all the cells, with the exception of cells attached to the bottom, were removed. The cells attached to the bottom were detached from the bottom using trypsin, and then collected by centrifugation. Then, the cells were suspended in a basal medium of low glucose DMEM containing 10% FBS, 1% L-glutamine and 1% penicillin-streptomycin and 4 ng/ml bFGF, and the suspended cells were seeded in a 100 mm cell culture plate. After 12~24 hours, the medium was replaced with fresh medium. It was found that the fetus-derived cell line in amniotic fluid showed heterogeneous populations (FIG. 1A: a-d), and had only a fibroblast-like morphology after two to three subcultures (FIG. 1A: e). When the cells had the morphology of FIG. 1, the medium was changed once every 2~3 days, and when the cells reached 80 to 90% confluence, subculture was performed.

EXAMPLE 2

Identification of Fetus-Derived Cells in Amniotic Fluid Via Karyotyping

In order to examine whether the cells are derived from the fetus in amniotic fluid, karyotyping was performed.

A karyotype shows the number, size, and shape of each chromosome type, and chromosome analysis is performed to detect mutations and to determine fetal sex. In order to perform karyotyping, the cell division was arrested at metaphase using colcemid for 1~2 hrs, and chromosome analysis was performed by G-banding staining. The karyotyping results showed that the fetus-derived cells in amniotic fluid had normal chromosomes and sex chromosomes of XY, indicating that the cells were derived from the fetus, not the mother (FIG. 2).

EXAMPLE 3

Analysis on Similarity Between Fetus-Derived Cells in Amniotic Fluid and Mesenchymal Stem Cells It was examined whether the fetus-derived cells in amniotic fluid have the characteristics of pluripotent mesenchymal stem cells.

Figure 3:
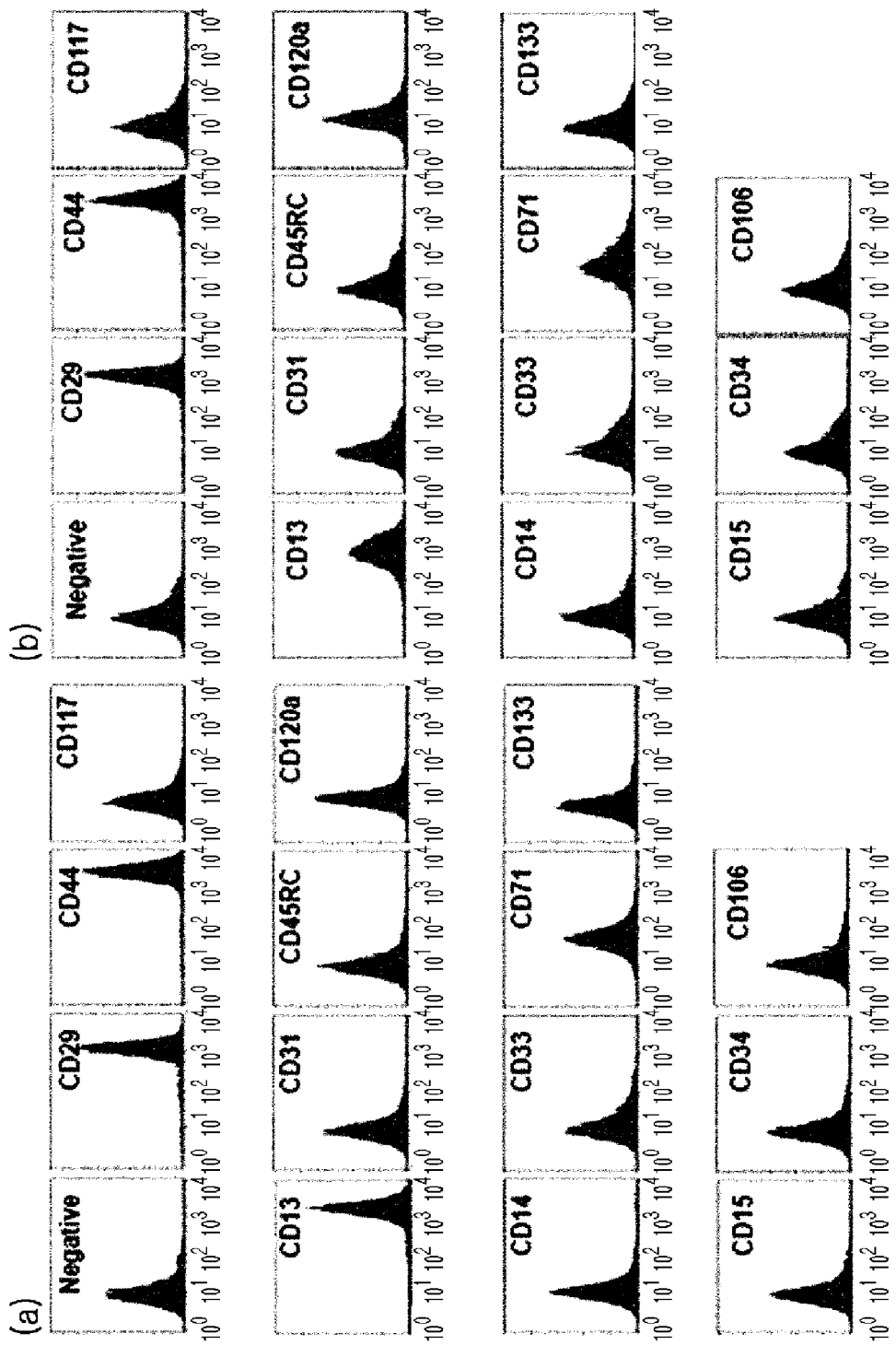
FIG. 3 shows the result of immune phenotyping using a flow cytometry, in which the fetus-derived cells in amniotic fluid (B) have similar characteristics to human bone marrow-derived mesenchymal stem cells (A)

First, when immune phenotyping was performed using a flow cytometry, expression of CD13, CD29, and CD44 were observed in the fetus-derived cells in amniotic fluid, compared to the human bone marrow-derived mesenchymal stem cells (FIG. 3). Although their expression is specific to the mesenchymal stem cells, each cell may show different characteristics. Thus, the capability to differentiate into osteoblasts, adipocytes, and chondrocytes, which is a representative characteristic of the mesenchymal stem cells, was examined.

The fetus-derived cells in amniotic fluid were differentiated like the human bone marrow-derived mesenchymal stem cells, and then osteogenic differentiation was demonstrated by the expression of osteopontin and osteocalcin, adipogenic differentiation was demonstrated by the expression of lipoprotein lipase (LPL), fatty acid binding protein 2 (aP2) and peroxisome proliferator-activated receptor gamma (PPARγ), and chondrogenic differentiation was demonstrated by the expression of Type II collagen, Type I collagen and aggrecan via reverse transcription-polymerase chain reaction (RT-PCR). Each differentiation was identified with the specific staining method: Calcification during osteogenic differentiation was identified with Alizarin Red S staining, accumulation of lipid droplets during adipogenic differentiation was identified with Oil red O staining, and the cartilage matrix during chondrogenic differentiation was identified with Alcian blue staining (FIG. 4). Therefore, the fetus-derived cells in amniotic fluid of the present invention were found to have similar characteristics to the bone marrow-derived mesenchymal stem cells.

EXAMPLE 4

Preparation of Conditioned Medium from Fetus-Derived Mesenchymal Stem Cells in Amniotic Fluid Preparation conditions for the conditioned media were established according to cell counts of the fetus-derived mesenchymal stem cells in amniotic fluid.

First, the established mesenchymal stem cells were detached from the bottom of 100 mm cell culture plate by trypsin treatment. The detached cells were collected and put in a 15 ml tube, followed by centrifugation. The collected cells were suspended in 5~10 ml of medium and mixed well. 20 μl of the floating cells in the tube was taken, and the number of cells was counted using a hematocytometer. Then, $5 \times 10^4$, $1 \times 10^5$, $2.5 \times 10^5$, and $5 \times 10^5$ cells were seeded in 100 mm cell culture plates containing the low glucose DMEM supplemented with 10% FBS, 1% L-glutamine and 1% penicillin-streptomycin and 4 ng/ml bFGF. After 12 hrs, the media were replaced with a DMEM/F12 serum-free conditioned media, and the cells were culture for 72 hrs. After 72 hrs, the culture medium of each cell count was transferred into a tube, followed by centrifugation. Filtration was performed using a 0.20 syringe filter to prepare conditioned media. After cultivation in the DMEM/F12 serum-free medium for 3 days, the morphology of the cells upon acquiring CM is shown in FIG. 5A. The cell counts per $cm^2$ were divided into four groups, and the cells were seeded to perform CFU-assay. The results showed that the highest value was observed in $100/cm^2$ and different patterns were observed according to the cell count per $cm^2$ (FIG. 5B).

EXAMPLE 5

Figure 6:
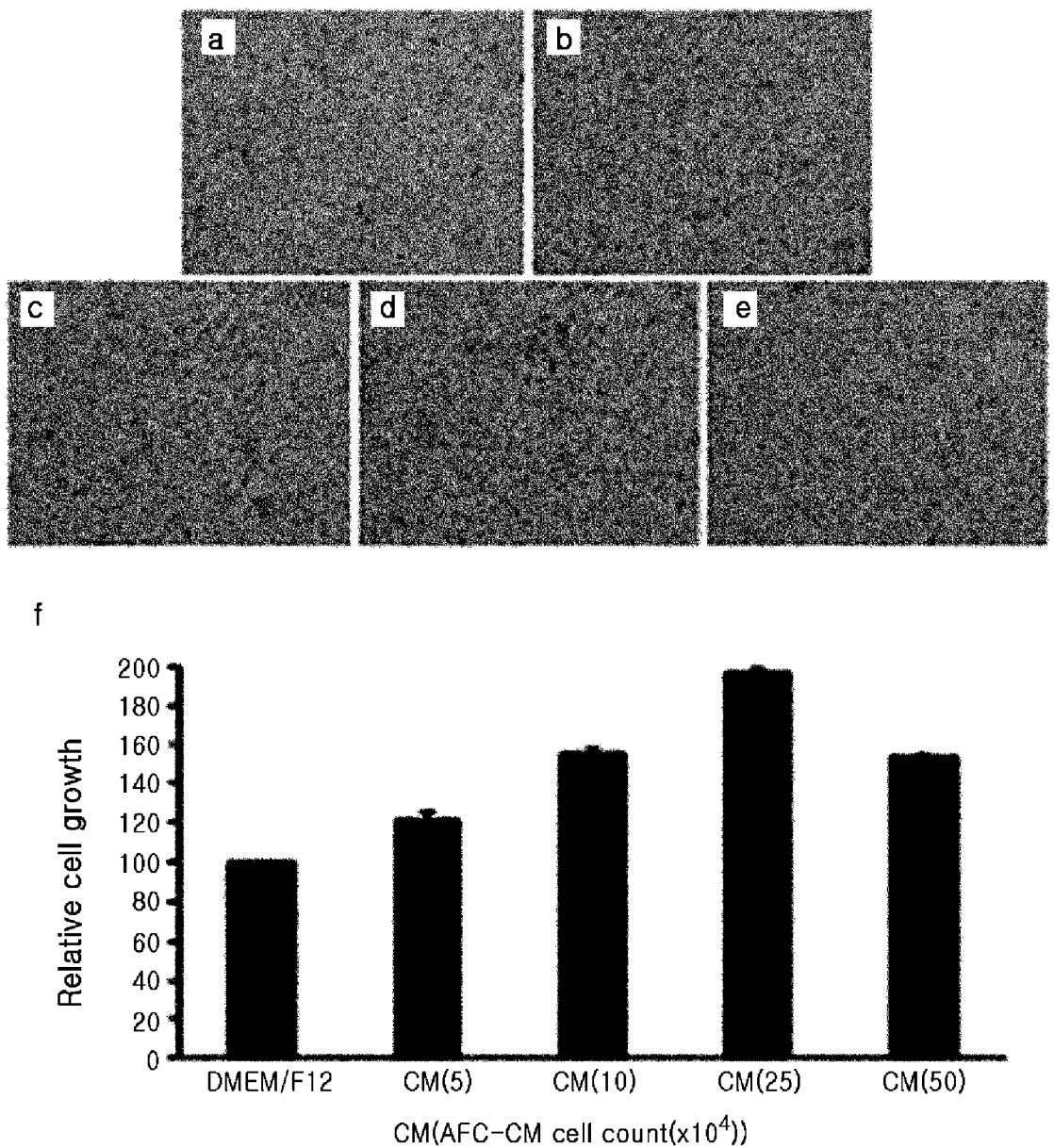
FIGS. 6 to 8 show the effects of plenty of growth factors, which are present in the conditioned medium obtained using the established fetus-derived mesenchymal stem cells in amniotic fluid, on fibroblast growth.
Figure 7:
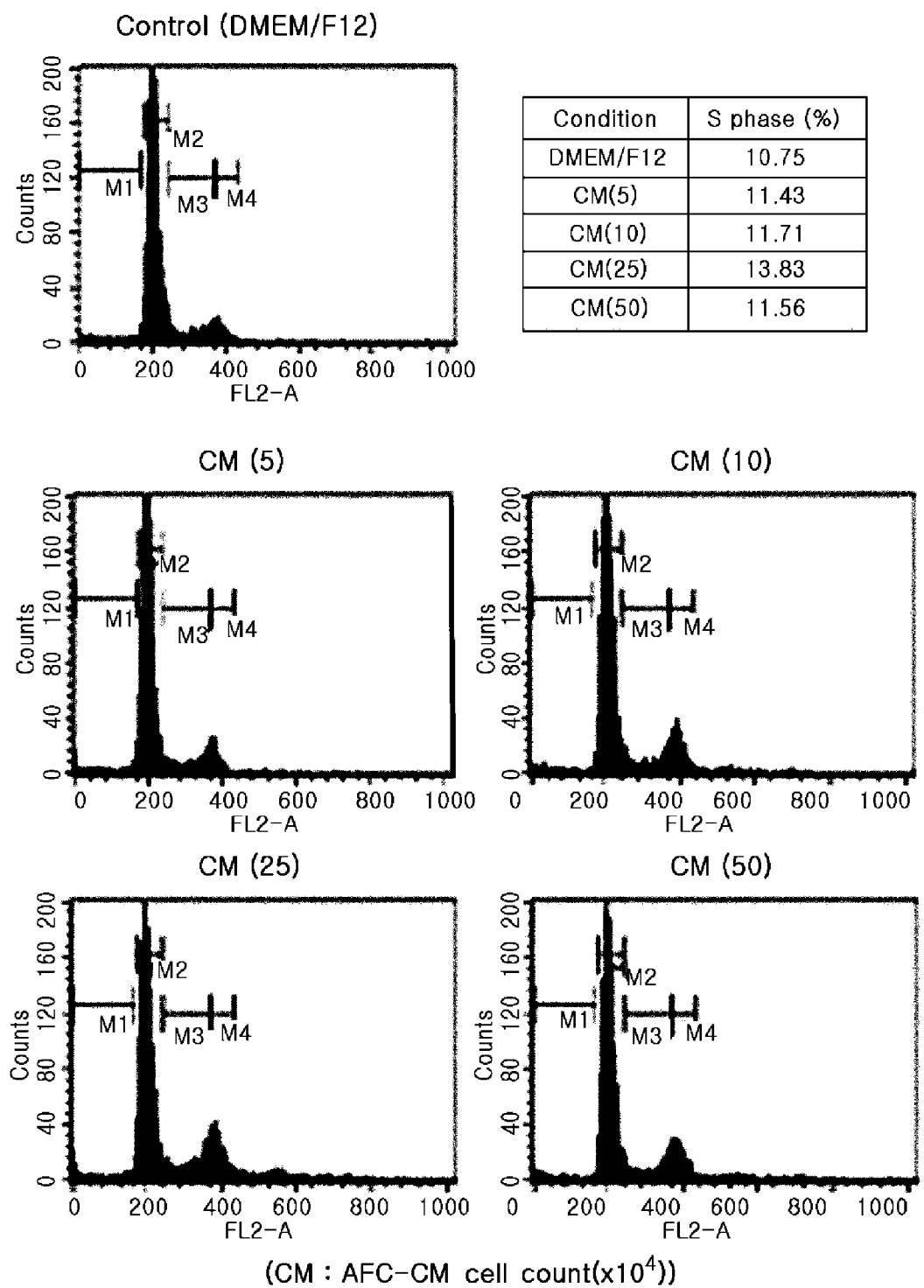
Figure 8:
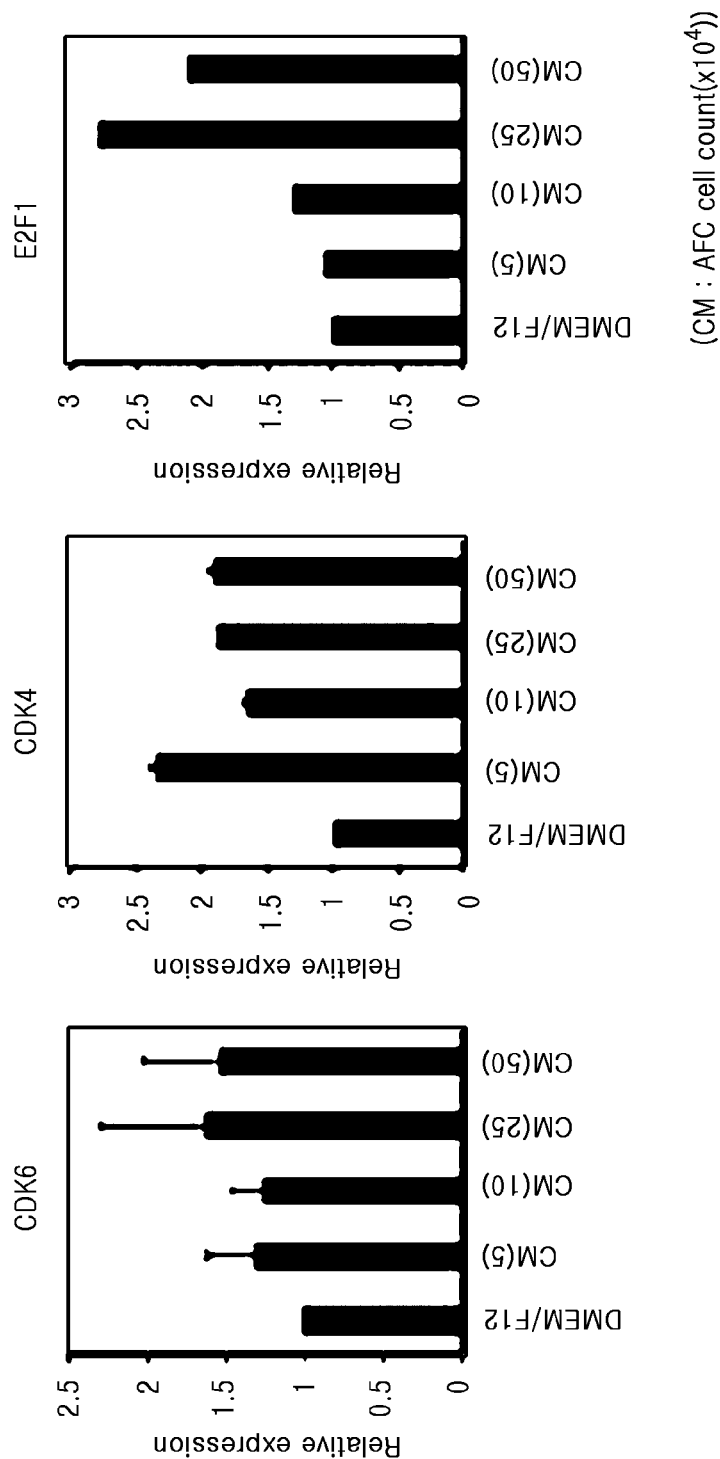

In Vitro Test on Effects of Conditioned Medium $5 \times 10^4$, $1 \times 10^5$, $2.5 \times 10^5$, and $5 \times 10^5$ of the fetus-derived mesenchymal stem cells in amniotic fluid were counted, and each of them was cultured in the DMEM/F12 serum-free medium for 3 days to prepare the conditioned media. In order to examine their effects on the fibroblast growth, the following experiment was performed. After cultivation in CM for 3 days, the cell morphology and growth were compared. The highest cell growth was observed in CM ($2.5 \times 10^5$) (FIG. 6). In order to demonstrate this result, after skin-derived fibroblasts were treated with CM, the cell growth cycle was identified with PI stain. As a result, the highest cell growth of 13.83% was observed at S phase (proliferation) in CM ($2.5 \times 10^5$), which is the same as that of the previous experiment (FIG. 7). Of the cell growth cycle, S phase-related gene expression was examined by Real-time PCR. The gene expression was found to be increased in the cells of the CM-treated group. Especially, high expression was observed in CM ($2.5 \times 10^5$), suggesting that CM derived from 250 thousands of amniotic fluid cells highly increases the cell growth (FIG. 8). On the basis of these experimental results, an increase in the expression of the cell growth-related proteins was examined to establish optimal culture conditions.

EXAMPLE 6

Figure 9:
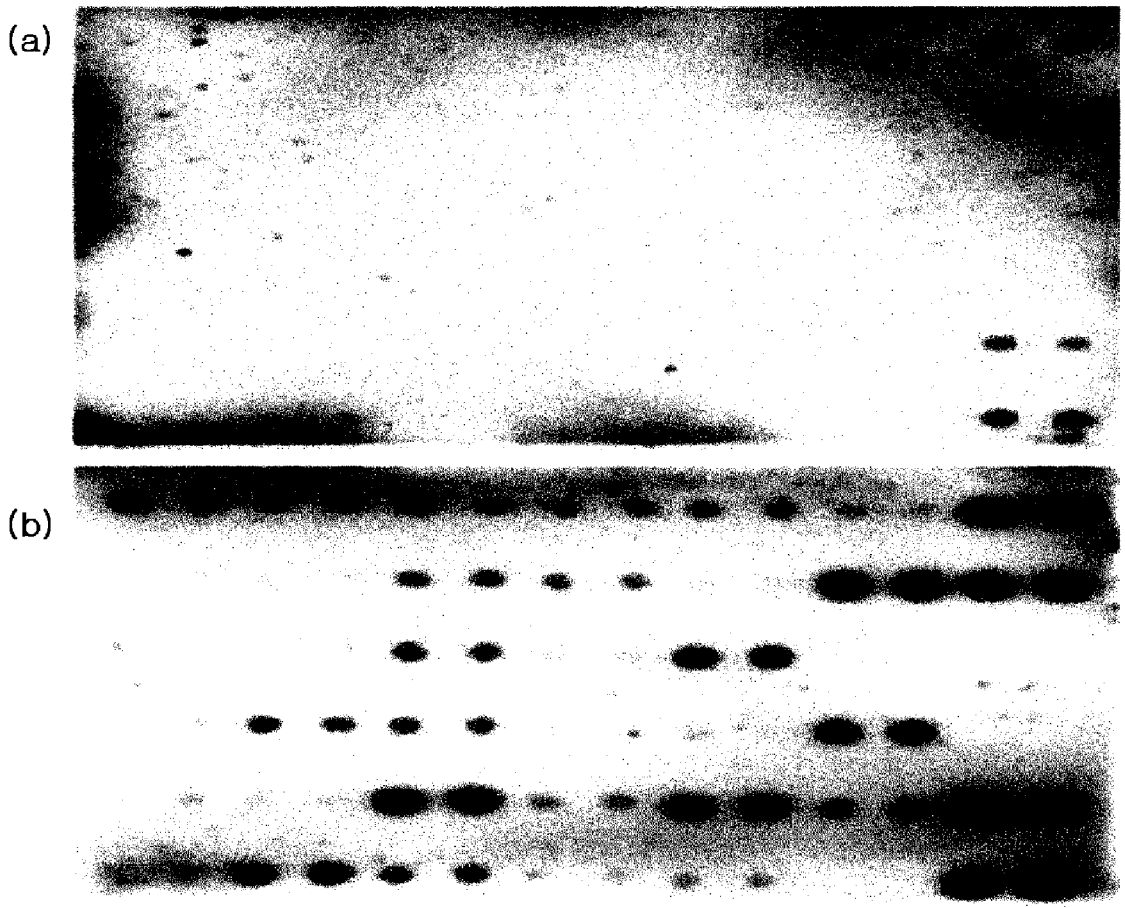
FIG. 9 shows the result of antibody array for analyzing the proteins in the conditioned medium obtained using the established fetus-derived mesenchymal stem cells in amniotic fluid, indicating that plenty of growth factors are produced in the medium ((A) DMEM/F12-serum free medium, (B) DMEM/F12-serum free conditioned medium)

Identification of Conditioned Medium Ingredients in Fetus-Derived Mesenchymal Stem Cells in Amniotic Fluid In order to analyze the ingredients of the conditioned medium obtained using the fetus-derived mesenchymal stem cells in amniotic fluid, changes in the amount of expressed proteins were examined by antibody array. Growth factor and protein expression were not observed in the DMEM/F12 serum-free medium (no conditioned medium) (FIG. 9A). The ingredients of the DMEM/F12 serum-free conditioned medium, were analyzed. As a result, it was found that 27 growth factors such as TGFβ, VEGF, EGF, TNFα, IL8, IL6, and MMP3 among total 36 cell growth factors and proteins involved in proliferation were included in the conditioned media (FIG. 9B).

EXAMPLE 7

Wound Healing Effect of Conditioned Medium in Skin Fibroblast

In order to examine whether the conditioned medium prepared using the amniotic fluid-derived stem cells shows wound healing effects, an artificial wound was generated in the skin-derived fibroblasts, and then the cells were treated with the conditioned medium. At 12 hrs, higher migration was observed in the conditioned medium-treated cells, and much higher in CM ($2.5×10^5$). In this connection, the relative migration rates were compared. The highest value was observed in the conditioned medium ($2.5×10^5$), indicating that the conditioned medium obtained using the amniotic fluid-derived stem cells has excellent wound healing effects (FIGS. 10 to 11). During measurement of the migration rate, expression of the genes involved in the wound healing was examined by Real-time PCR. The highest quantitative expression was observed in the conditioned medium ($2.5×10^5$), compared to DMEM/F12 serum-free medium (no conditioned medium), indicating that the conditioned medium derived from 250 thousands of amniotic fluid cells shows the highest wound healing effects (FIG. 11).

EXAMPLE 8

Skin Regeneration Effects of Conditioned Medium in Mouse In Vivo

It was examined whether the conditioned medium of the fetus-derived mesenchymal stem cells in amniotic fluid shows skin regeneration effects on the skin-wounded mouse. The mouse skin was artificially wounded by punching of 29-30 mm$^2$, and then treated with the general DMEM/F12 serum-free medium and the conditioned DMEM/F12 serum-free medium, and the wound closure was observed. Up to 8 days, skin regeneration was not observed in the wound site treated with the general DMEM/F12 serum-free medium, but the wound site treated with the conditioned DMEM/F12 serum-free medium was found to be gradually reduced (FIG. 12A). The measured values of wound closure are shown in a graph (FIG. 12B).

EXAMPLE 9

Examination of Conditioned Medium Effect by Clinical Study

Figure 13:
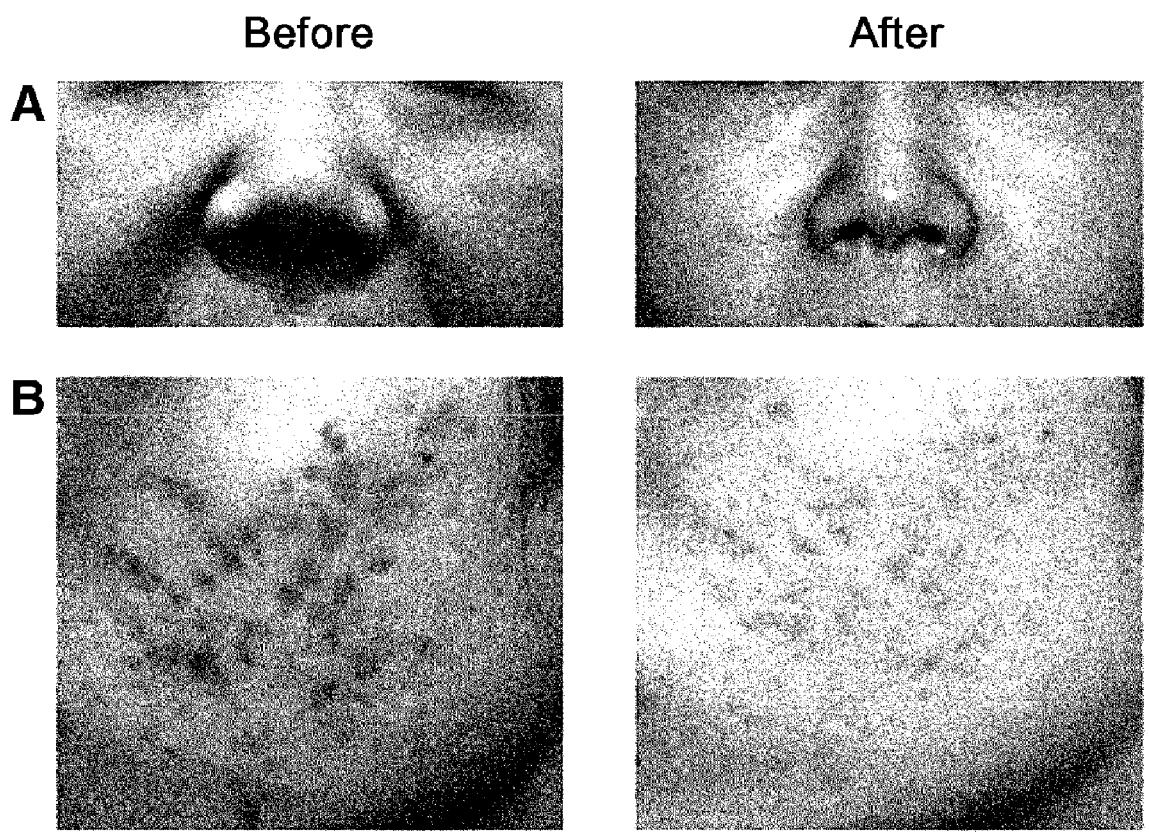
FIG. 13 shows the result of clinical study, indicating the conditioned medium obtained using the fetus-derived mesenchymal stem cells in amniotic fluid having regeneration effects.

The conditioned medium of the fetus-derived mesenchymal stem cells in amniotic fluid was used in a clinical study to examine its skin regeneration effects. The skin was stimulated using a microneedle after microtherapy of the conditioned medium once a week. After 8 weeks, it was observed that skin elasticity improved, skin tone became brighter, and fine wrinkles were reduced, and skin pores were minimized (FIG. 13A). When the observation was performed in the same manner for 6~7 weeks, the improvement in red-marks of acne scars and rapid wound regeneration were observed (FIG. 13B).

EFFECT OF THE INVENTION

In the present invention, the cells derived from the fetus in amniotic fluid are cultured to obtain pluripotent mesenchymal stem cells, and thus another source of mesenchymal stem cells is provided, in addition to the bone marrow. That is, the present invention suggests a possibility of the cells derived from the fetus in amniotic fluid as a pluripotent mesenchymal stem cell, and a conditioned medium is prepared using the fetus-derived mesenchymal stem cells in amniotic fluid, thereby providing an excellent composition for improving cell growth and skin regeneration.

What is claimed is:

1. A method for improving a skin condition of a subject, the method comprising contacting the skin of the subject with a conditioned culture medium, wherein the conditioned culture medium is obtained by culturing fetus-derived mesenchymal stem cells obtained from amniotic fluid in culture medium, and wherein the skin condition is, wrinkles, skin damages caused by UV rays, skin wound, or skin lifting.

2. The method according to claim 1, wherein the fetus-derived mesenchymal stem cells have the following characteristics:
   (a) showing the immunological characteristics of being all positive for CD13, CD29 and CD44;
   (b) growing and adhering to cell culture plates and showing a spindle-shaped morphology; and
   (c) having a capacity to differentiate into mesodermal cell lineages.

3. The method according to claim 1, wherein the conditioned culture medium comprises Apo-1/Fas, epidermal growth factor (EGF), IP-10(Interferon-γ inducible protein-10), Leptin, MIP4, MMP3, Rantes, interferon-gamma (IFNγ), human transforming growth factor (TGF-β), tumor necrosis factor-alpha (TNFα), tumor necrosis factor receptor I (TNFRI), tumor necrosis factor receptor II (TNFRII), intracellular adhesion molecule-1 (ICAM-1), vascular cell adhesion molecule-1 (VCAM-1), vascular endothelial growth factor (VEGF), interleukin-1beta (IL-β), interleukin-1 receptor alpha (IL-1Rα), IL-2, IL-3, IL-4, IL-5, IL-6, IL-6R, IL-7, IL-8, IL-12 and IL-15.

4. The method according to claim 1, wherein the conditioned culture medium is contained in a cosmetic composition.

5. The method according to claim 4, wherein the composition has a formulation selected from the group consisting of a solution, a suspension, an emulsion, a paste, a gel, a cream, a lotion, a powder, a soap, a surfactant-containing cleanser, an oil, a powdered foundation, an emulsion foundation, a wax foundation, and a spray.

6. The method according to claim 1, wherein the conditioned culture medium is contained in a pharmaceutical composition.

7. The method according to claim 1, wherein the conditioned culture medium is prepared by comprising:
   (a) isolating the fetus-derived cells in amniotic fluid that is obtained from a pregnant woman;
   (b) subculturing the cells in a medium supplemented with FBS and bFGF so as to obtain the fetus-derived mesenchymal stem cells;
   (c) culturing the obtained fetus-derived mesenchymal stem cells in a serum-free medium for 1 to 10 days so as to prepare a conditioned medium; and
   (d) collecting the conditioned culture medium.

* * * * *

UNITED STATES PATENT AND TRADEMARK OFFICE
CERTIFICATE OF CORRECTION

PATENT NO. : 8,586,540 B2  
APPLICATION NO. : 13/257623  
DATED : November 19, 2013  
INVENTOR(S) : Lee et al.

Page 1 of 1

It is certified that error appears in the above-identified patent and that said Letters Patent is hereby corrected as shown below:

On the Title Page

Item [75] Inventors:
"SeungkWon You, Gyeonggi-do (KR); Byung Sun Yoon, Seoul (KR); Jai-Hee Moon, Seoul (KR); Eun Kyoung Jun, Gyeonggi-do (KR); Jonggun Kim, Seoul (KR); Hye-Youn Jung, Daejon (KR); Jung Han Lee, Seoul (KR); Eulsoon Park, Seoul (KR); Isaac Maeng, Gyeonggi-do (KR); Jun Sung Kim, Gyeonggi-do (KR); Jang Ho Lee, Seoul (KR); HWang Heui Lee, Seoul (KR); Jong Won Lee, Gyeonggi-do (KR); Kyoung Shik Cho, Seoul (KR)"

should read:
--"Jang Ho Lee, Seoul (KR); SeungkWon You, Gyeonggi-do (KR); Byung Sun Yoon, Seoul (KR); Jai-Hee Moon, Seoul (KR); Eun Kyoung Jun, Gyeonggi-do (KR); Jonggun Kim, Seoul (KR); Hye-Youn Jung, Daejon (KR); Jung Han Lee, Seoul (KR); Eulsoon Park, Seoul (KR); Isaac Maeng, Gyeonggi-do (KR); Jun Sung Kim, Gyeonggi-do (KR); HWang Heui Lee, Seoul (KR); Jong Won Lee, Gyeonggi-do (KR); Kyoung Shik Cho, Seoul (KR)"--

Signed and Sealed this  
Eighteenth Day of February, 2014

Michelle K. Lee  
*Deputy Director of the United States Patent and Trademark Office*